(12) United States Patent
Spiegel et al.

(10) Patent No.: US 7,309,055 B1
(45) Date of Patent: Dec. 18, 2007

(54) APPARATUS FOR FLUSHING FLUIDS FROM A TUBE

(76) Inventors: Aldona J. Spiegel, 2514A South Blvd., Houston, TX (US) 77098; Robert S. Troxclair, 17911 Cali Dr., Houston, TX (US) 77090

( * ) Notice: Subject to any disclaimer, the term of this patent is extended or adjusted under 35 U.S.C. 154(b) by 519 days.

(21) Appl. No.: 10/934,536

(22) Filed: Sep. 7, 2004

(51) Int. Cl.
    *F16K 7/04* (2006.01)
(52) U.S. Cl. .................. 251/6; 222/102; 417/477.6
(58) Field of Classification Search ............ 251/4–10; 604/65–67, 118–129, 244–262, 27; 222/101, 222/102, 105; 417/477.6, 467
    See application file for complete search history.

(56) References Cited

U.S. PATENT DOCUMENTS

| | | | |
|---|---|---|---|
| 91,210 A * | 6/1869 | Carter .................. 100/151 |
| 829,516 A * | 8/1906 | Earle .................. 222/371 |
| 2,245,030 A | 6/1941 | Gottesfeld et al. | |
| 2,530,327 A * | 11/1950 | Derrick .................. 222/102 |
| 2,554,217 A * | 5/1951 | Shaw .................. 222/102 |
| 2,712,335 A * | 7/1955 | Houldsworth ............ 224/631 |
| 3,194,452 A * | 7/1965 | Sanderford ............. 222/407 |
| 3,297,205 A * | 1/1967 | Sumner ................. 222/102 |
| 3,648,701 A | 3/1972 | Botts | |
| 3,831,625 A * | 8/1974 | Roediger ............... 137/377 |
| 3,847,370 A * | 11/1974 | Engelsher .............. 251/6 |
| 4,164,223 A | 8/1979 | Munib | |
| 4,266,751 A | 5/1981 | Akhavi | |
| 4,393,873 A * | 7/1983 | Nawash et al. ......... 604/151 |
| 4,563,171 A | 1/1986 | Bodicky | |
| 4,805,805 A * | 2/1989 | Ocheskey .............. 222/102 |
| 4,856,755 A * | 8/1989 | Clarke ................. 251/6 |
| 5,052,900 A * | 10/1991 | Austin ................. 417/309 |
| 5,118,011 A * | 6/1992 | Kopp .................. 222/102 |
| 5,336,203 A * | 8/1994 | Goldhardt et al. ....... 604/247 |
| 5,441,172 A * | 8/1995 | Yu .................... 222/52 |
| 5,881,916 A | 3/1999 | Madjarac | |
| 6,129,330 A | 10/2000 | Guala | |
| 6,296,150 B1 | 10/2001 | Farris | |
| 6,364,204 B1 * | 4/2002 | Thomas ................ 232/43.5 |

* cited by examiner

*Primary Examiner*—Gregory Huson
*Assistant Examiner*—Andrew Rost
(74) *Attorney, Agent, or Firm*—Egbert Law Offices

(57) ABSTRACT

A tube flushing device has a shell having a first housing and a second housing connected on a side thereof so as to be movable between an open position and a closed position. A first pair of wheels are rotatably mounted in the first housing. A second pair of wheels rotatably mounted in the second housing. The first pair of wheels engages the second pair of wheels when the housings are in the closed position. The shell has openings on opposite ends thereof. A tube can extend through the openings and between the first and second pair of wheels so as to allow fluids therein to be flushed therefrom as the shell moves along the length of the tube.

14 Claims, 4 Drawing Sheets

APPARATUS FOR FLUSHING FLUIDS FROM A TUBE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to tube flushing devices. More particularly, the present invention relates to mechanical devices that push and compress flexible tubing so as to urge fluids from one location in the tubing toward another location of the tubing. The present invention also relates to fluid collecting bulbs that are connected to an end of such tubing.

BACKGROUND OF THE INVENTION

Tubing is used extensively in hospitals to convey fluids for various purposes including introducing fluids into the body and withdrawing fluids from the body. In body fluid drainage systems, for example, in chest drainage apparatus, an elastomeric tube is connected at one end to a chest drainage catheter connected to the plural cavity of the patient. The opposite end of the tube is connected to a fluid drainage collection bottle, bulb, or chamber. Such drainage apparatus may collect drainage either by the effects of gravity alone or by vacuum assist.

In such chest drainage systems, fibrin or a blood clot may occlude the tube or restrict the fluid discharge rate of flow. It has been common practice for the attendant to displace or clear the contents of the tube and remove the obstruction by hand. Because the tubing is generally made of a material which produces an outer surface with a relatively high coefficient of friction, such as polyvinyl chloride, latex, polyurethane or silicone, the fingers are generally first lubricated by applying an oil or grease to them. Then, while squeezing and compressing the tube between the fingers, the fingers are advanced longitudinally along the tube to move fluid and other matter through the tube thereby removing the obstruction or increasing the fluid flow rate. Clearing solids, semi-solids or liquids from resilient flexible tubing in various other fluid systems is often accomplished in a similar manner. If a lubricant is not employed, the friction between the fingers and tubing would cause chaffing of the skin. Even when a lubricant is used, some chaffing of the skin occurs and the tubing may not be cleared as well as it should be. Also, the use of lubricants is time consuming since it requires the application, as well as, removal of the lubricant from the hand.

In order to avoid the above-identified problems associated with the stripping or clearing the contents of tubing, various hand tools having rollers have been proposed. The tubing is clamped between the rollers and then the rollers are moved longitudinally along the tubing to move the tubing contents longitudinally therealong. For example, U.S. Pat. No. 5,881,916, issued on Mar. 16, 1999 to M. G. Madjarac, describes a tube unclogging device which has a first roller mounted on one side of a U-shaped body and another roller mounted on an opposite side of the U-shaped body. The U-shaped body is suitably flexible so that the application of force onto the outer surfaces of the U-shaped body will cause the rollers on one side of the body to be pushed toward the rollers on the opposite side of the body. As a result, a tube can be placed between the rollers. The movement of the rollers along the length of the tube will cause the liquids in the tube be expressed outwardly therefrom.

U.S. Pat. No. 4,266,751, issued on May 12, 1981 to D. S. Akahavi, teaches the use of a pair of rollers that are flexibly connected together. The rollers can be applied over the length of the tube for the purposes of expressing the contents of the tube. The roller is moved in a direction with thumb motion across another roller and across an adjacent table surface longitudinally disposed relative to the roller in a top arm. A clamp advances toward a blood analyzing machine without buckling the tubular reservoir. The device is useful for one-handed movement toward a dispensing end of a flexible tube blood reservoir.

U.S. Pat. No. 4,164,223 teaches another type of item having a pair of hinged rollers which are used to flush tubes. The instrument is for use with surgical procedures, such as clearing and dislodging the contents of chest tubing, catheters, common duct T-tubing and IV tubing. The pair of rollers are mounted on shafts which are hinged together at one end. A cylindrical handle is mounted on the opposite end of one shaft. An opposed thumb rest is mounted on the end of the other shaft. The hand of the user grasps the handle and the thumb rest for moving the rollers into and out of engagement with opposite sides of the tubing. The instrument compresses the tubing and is moved a desired distance along its length for propelling tubing contents.

U.S. Pat. No. 2,245,030, issued on Jun. 10, 1941 to Gottesfeld et al., teaches a portable pair of rollers that are used for flushing fluid-bearing tubes.

U.S. Pat. No. 6,296,150, issued on Oct. 2, 2001 to B. Farris, describes the use of a pair of rollers with a hinge that allows the rollers to open for the purposes of placing a tube between the rollers.

U.S. Pat. No. 3,648,701, issued on Mar. 14, 1972 to M. Botts, describes a forcep instrument for striping the contents of flexible tubes. One arm of the forceps has a roller mounted thereon. Another arm of the forceps also has another roller resiliently mounted thereon. The closing of the forceps will create a compressive force upon the tubing for the purposes of flushing fluid from the tubing.

U.S. Pat. No. 4,563,171, issued on Jan. 7, 1986 to R. O. Bodicky, describes an apparatus for conveying fluids through a tubing. A tube clearing sleeve surrounds the tubing. The sleeve has a slick inner surface and a coefficient of friction less than the outer surface of the tubing. The sleeve is compressed between the fingers to compress the tubing and the compressed sleeve is advanced along the tubing to displace contents in the tubing.

U.S. Pat. No. 6,129,330, issued on Oct. 10, 2000 to G. Guala, describes a roller clamp that is used for regulating fluid flow through an elastically deformable tubing. A roller adjustably resides over a surface of the tubing so as to suitably compress the tubing for controlling fluid flow.

It is an object of the present invention to provide a device for removing fluid from tubing.

It is another object of the present invention to provide a fluid stripping device that is relatively compact, easy to use and inexpensive.

It is another object of the present invention to provide a fluid flushing apparatus that is self-locking upon the tube.

It is another object of the present invention to provide a fluid removing device that effectively prevents air from passing into the tubing during the stripping operation.

It is a further object of the present invention to provide a tube flushing device which includes wheel which will not slide on the tube and will not kink the tube.

It is another object of the present invention to provide a tube flushing apparatus which maintains the tube in line during the flushing of the tubing.

It a further object of the present invention to provide an apparatus which can maintain a fluid-receiving bulb in proximity to the human body.

It is another object of the present invention to provide an apparatus in which multiple fluid-receiving bulbs can be organized and matched to receiving pouches.

It is a further object of the present invention to provide an apparatus which allows the user to properly sleep, walk, shower, and carry out daily activities without interference by a hanging fluid-receiving bulb.

It is a further object of the present invention to provide an apparatus which prevents gravity, or other pulling forces, from affecting the fluid-receiving bulb.

It is a further object of the present invention to provide an apparatus whereby an end of the tube can be securely affixed by stitches to the human body.

It is another object of the present invention to provide an apparatus whereby air is prevented from entering the human body while not reducing the flow the drain tube.

It is still another object of the present invention to provide an apparatus which is easy to use, relatively inexpensive, easy to manufacture and disposable.

These and other objects and advantages of the present invention will become apparent from a reading of the attached specification and appended claims.

BRIEF SUMMARY OF THE INVENTION

The present invention is a tube flushing device comprising a shell having a first housing and a second housing hingedly connected on a side thereof so as to be movable between an open position and a closed position. A first pair of wheels are rotatably mounted in the first housing so as to extend transversely to a longitudinal axis of the first housing. A second pair of wheels are rotatably mounted in the second housing so as to extend transversely to a longitudinal axis of the second housing. The first pair of wheels are in an aligned relationship with the second pair of wheels when the first and second housings are in the closed position. The shell has an opening at one longitudinal end thereof and an opening at an opposite longitudinal end thereof.

In the present invention, the first pair of wheels are mounted at opposite ends of a leaf spring. The leaf spring is secured within the first housing of the shell. Each of the first pair of wheels has a generally convex shape. Each of the second pair of wheels has a generally concave shape. Each of the first pair of wheels has a central rubber wheel portion extending therearound. The first pair of wheels has beveled sides extending outwardly on opposite sides of the rubber wheel portion. The second pair of wheels has a pair of flexible flanges extending outwardly on respective opposite sides of a central portion thereof. The beveled sides contact the flexible flanges when the first and second housings are in the closed position.

In the shell of the present invention, each of the openings at opposite ends thereof includes a first funnel portion formed on one of the first and second housings and a second funnel portion formed on the other of the first and second housings. The first and second funnel portions form a complete funnel having a wide end at the end of the shell. This funnel extends inwardly and narrows into an interior of the shell when the first and second housings are in the closed position.

In the present invention, a guide member is positioned between the second pair of wheels in the shell. This guide member has a slot aligned with the second pair of wheels. The slot has a width generally matching a diameter of a tube extending between the second pair of wheels. A first U-shaped bracket is affixed to one end of the leaf spring. A second U-shaped bracket is affixed to an opposite end of the leaf spring. One of the first pair of wheels is rotatably mounted in the first U-shaped bracket. Another of the first pair of wheels is rotatably mounted in the second U-shaped bracket. The first pair of wheels are flexibly positioned within the shell.

In the present invention, the shell has a latch means formed thereon. This latch means serves to releasably retain the first and second housings in the closed position. The latch means specifically includes a slot formed through a wall of the first housing and an arm with hook member affixed within the second housing. The arm has a button extending outwardly of the shell. The button is movable between a position allowing the hook member to engage the slot and a second position releasing the hook member from the slot.

The first housing has a pair of wheel wells formed adjacent opposite ends thereof. These wheel wells correspond in location to the first pair of wheel in the first housing. The pair of wheel wells accommodate the flexible movement of the first pair of wheels in the first housing. The shell has a first gripping area defined between this pair of wheel wells on the first housing. The shell has a second gripping area defined on an opposite side of the shell.

In the apparatus of the present invention, a tube extends between the first pair of wheels and the second pair of wheels when the first and second housings are in the closed position. The tube extends through the openings at the end of the shell. The first and second pair of wheels compress the tube when the first and second housings are in the closed position so as to push fluids outwardly through the tube as the shell moves along a length of the tube. A fluid-collecting bulb is affixed to an end of the tube. The shell is movable toward the bulb so as to push the fluid into the bulb. A bulb-receiving pouch has the bulb removably received therein. A means for securing is connected to the pouch so as to allow the pouch to be retained on a human body such that the bulb is also retained in proximity to the human body. The pouch can include a first plurality of pouches affixed in side-by-side relation. The means for securing is an elastic belt positioned adjacent an upper opening of the first plurality of pouches. The bulb can also include a plurality of bulbs. The plurality of bulbs are respectively received in the plurality of pouches. Each of the bulbs has an alphanumeric indicia thereon. Each of the plurality of pouches also has an alphanumeric indicia thereon corresponding to the alphanumeric indicia of the bulbs. The pouches are formed of a see-through material, such as transparent plastic or mesh material. A second plurality of pouches can be removably affixed to an opposite side of the first plurality of pouches from the belt.

The apparatus of the present invention also includes a gasket member affixed adjacent an opposite end of the tube from the bulb. The gasket member has a concave portion at one side thereof. The gasket member also a notch extending therearound. The gasket member is of a material that has a greater rigidity than a rigidity of the tube. The gasket member also a peripheral ring extending outwardly thereof on a side opposite the concave portion. The peripheral ring has a plurality of holes formed therearound and therethrough. Each of the plurality of holes has a diameter suitable for allowing a stitching needle to pass therethrough.

DETAILED DESCRIPTION OF THE INVENTION

Figure 1:
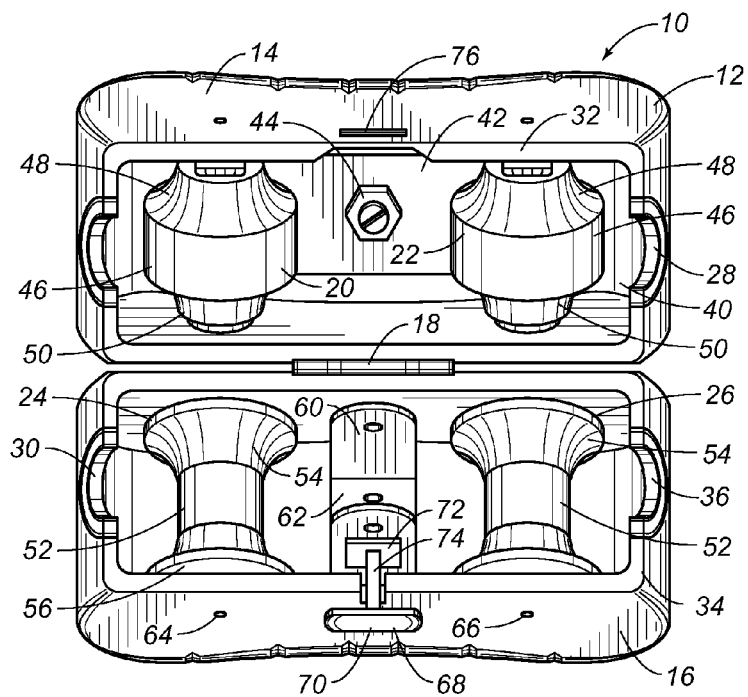
FIG. 1 is a side elevational view showing the apparatus of the present invention with the housings in the open position.

Referring to FIG. 1, there is shown the fluid removal apparatus 10 in accordance with the teachings of the present invention. The fluid removal apparatus 10 includes a shell 12 having a first housing 14 and a second housing 16 hingedly connected by hinge 18 together on one side of the shell 12. A first pair of wheels 20 and 22 are rotatably mounted in the first housing 14 so as to extend transverse to a longitudinal axis of the first housing 14. A second pair of wheels 24 and 26 are rotatably mounted in the second housing 16 so as to extend transverse to a longitudinal axis of the second housing 16. As will be described hereinafter, the first pair of wheels 20 and 22 respectively engage the second pair of wheels 24 and 26 when the first housing 14 and the second housing 16 are in a closed position. The shell 12 has an opening 28 at one end thereof and an opening at an opposite end thereof.

As can be seen in FIG. 1, the shell 12 has a first housing 14 of a similar shape as the second housing 16. The first housing 14 will close such that edge 32 is in surface-to-surface contact with the edge 34 of the second housing 16. The opening 28 defines a funnel portion with the opening 36 on the second housing 16. When the housings 14 and 16 are closed together, the funnel portions 28 and 36 will form a complete funnel which narrows inwardly into the interior 40 of the shell 12. A similar configuration relates to the opening 30 at the opposite end of the shell 12.

The first pair of wheels 20 and 22 are mounted to a leaf spring 42 on the interior of the first housing 14. The first pair of wheels 20 and 22 have a generally convex shape. The rollers 20 and 22 are rotatably mounted to U-shaped brackets formed on the leaf spring 42 (and described in greater detail in FIGS. 7 and 8). A nut 44 engages the leaf spring 42 so as to be affixed to the leaf spring 42. A suitable bolt, or other fastener, can be used so as to affix the leaf spring 42 within housing 14. The leaf spring 42 is intended to provided balanced pressures exerted by the first pair of wheels 20 and 22 during the stripping action on a tube interposed between the wheels 20 and 22 and the wheels 24 and 26.

The wheels 20 and 22 have a central rubber wheel portion 46 extending therearound. The wheels 20 and 22 have beveled sides 48 and 50 extending outwardly on opposite sides of the central rubber wheel portion 46.

The second pair of wheels 24 and 26 have a central rubber wheel portion 52 formed between a pair of flexible flanges 54 and 56. The beveled sides 48 and 50 will contact the flexible flanges 54 and 56 when the first housing 14 is in its closed position with respect to the second housing 16. The second pair of wheels 24 and 26 have a generally concave shape with a generally flat surface formed by the rubber portion 52. The rubber wheel portion 46 of the first pair of wheels 20 and 22 will come into close proximity with the rubber wheel portion 52 of the second pair of wheels 24 and 26 when the shell 12 is in its closed position. A guide member 60 is positioned between the wheels 24 and 26 in the second housing 16. The guide member 60 has a slot 62 formed therein. The slot 62 will have a width generally matching a diameter of a tube extending between the wheels 24 and 26. The guide member 60 serves to assure that alignment of the tube is constantly maintained through the interior of the shell 12.

In FIG. 1, it can be seen that the wheels 24 and 26 are rotatably mounted on axles 64 and 66. Axles 64 and 66 are supported on opposite sides of the housing 16. The latch member 68 is also positioned on the second housing 16 so as to have a button 70 extending outwardly therefrom. A hook member 72 is mounted on an arm 74 so as to be movable relative to the movement of the button 70. Hook member 72 is suitable for engaging slot 76 on the first housing 14 when the shell 12 is in its closed position. As such, the relationship between the hook member 72 and slot 76 will provide a positive locking force when the shell 12 is in its closed position.

Figure 2:
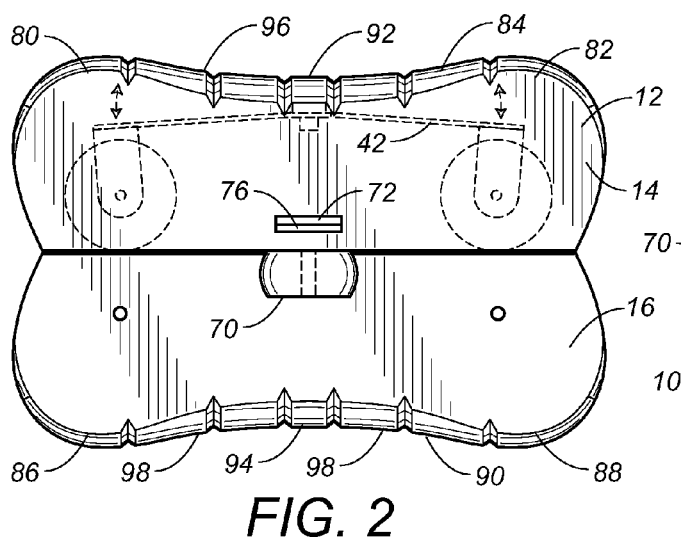
FIG. 2 is a side elevational view of the apparatus of the present invention with the housings in the closed position.

FIG. 2 shows the shell 12 in its closed position in which the housing 14 is juxtaposed against the housing 16. In FIG. 2, it can be seen that wheel wells 80 and 82 are formed along the top surface 84 of the first housing 14. Similarly, wheel wells 86 and 88 are formed on an opposite end of the bottom surface 90 of the second housing 16. Wheel wells 80, 82, 86 and 88 are intended to accommodate the flexible movement of the respective wheels on the interior 40 of the shell 12. As a result, the shell 12 can be of a more compact configuration. A slightly indented gripping area 92 is formed on the top surface 84 of the first housing 14. A similar indented gripping area 94 is formed on the underside 90 of the second housing 16. A plurality of ribs 96 are formed in parallel relationship along the top side 84 of the first housing 14. Similarly, a plurality of ribs 98 are also formed along the underside 90 of the second housing 16. The ribs 96 and 98, along with the indented configuration of the gripping areas 92 and 94, assures a positive retaining force when the thumb and index finger are applied onto the first housing 14 and the second housing 16.

In FIG. 2, it can be seen how the wheel 20 is retained by leaf spring 42 on the interior of the first housing 14. Arrow 100 illustrates the flexible movement of the first wheel 20 relative to the leaf spring 42. The wheel well 80 is suitably positioned so as to accommodate this flexible movement of the wheel 20. Because of the flexible movement provided by the leaf spring 42 between the wheels 20 and 22, variations in pressure during the movement of the shell 12 along the length of a tube can be accommodated.

FIG. 2 shows that the hook member 72 is engaged within the slot 76. The button 70 extends outwardly of the surface of the second housing 16. As a result, the hook member 72 positively retains the first housing 14 in juxtaposition against the second housing 16.

Figure 3:
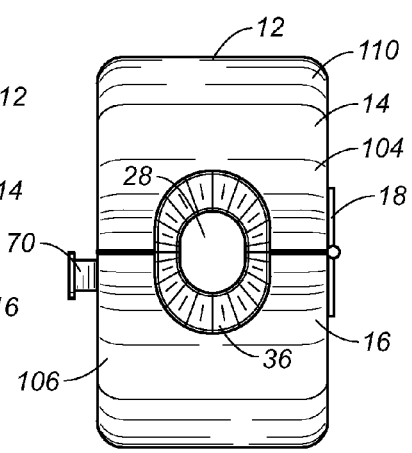
FIG. 3 is an end view of the apparatus of the present invention.

FIG. 3 shows an end view of the shell 12. As can be seen, the button 70 extends outwardly on one side of the shell 12. The hinge 18 is illustrated as affixed to the first housing 14 and to the second housing 16 on an opposite side 104 of the shell 12 from the side 106 from which button 70 extends. FIG. 3 also shows how the first funnel portion 108 is arranged relative to the second funnel portion 36 of the opening 28 at the end 110 of the shell 12. The first funnel portion 108 is approximately one-third of the diameter of the complete funnel formed at opening 28. The second funnel portion 36 is approximately two-thirds of the entire funnel formed at the opening 28. When joined together by the closing of first housing 14 with respect to the second housing 16, the opening 28 for the introduction of the tube is formed. The complete funnel formed by funnel portions 36 and 108 will narrow into the interior of the shell 12.

Figure 4:
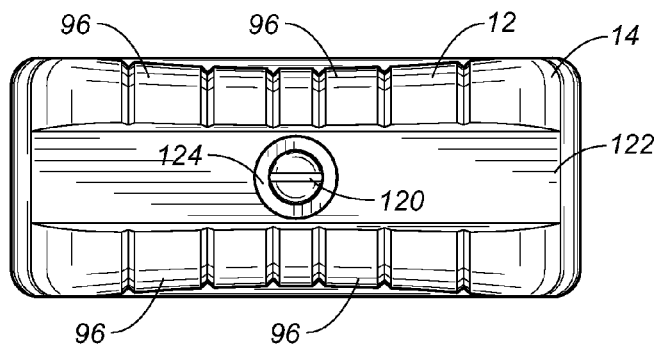
FIG. 4 is a plan view of the apparatus of the present invention.

FIG. 3 shows a top view of the first housing 14 of shell 12. In FIG. 4, it can be seen how the ribs 96 are formed along the indented area 92 at the top of the shell 12. A bolt head 120 extends outwardly of a slot 122 formed between the sides of the shell 12. Bolt 120 extends into the interior 40 of the shell 12 so as to engage with the nut 44 associated with the leaf spring 42. A suitable washer 124 can be interposed between the surface of slotted area 122 and the head of bolt 120.

Figure 5:
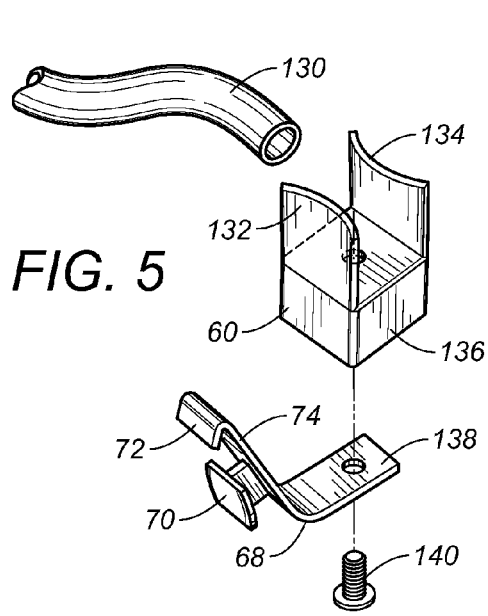
FIG. 5 is an exploded showing the guide and latch members of the apparatus of the present invention.

FIG. 5 illustrates the manner in which the guide member 60 serves to receive tube 130. The guide member 60 has inwardly curved walls 132 and 134 supported upon a frame section 136. The walls 132 and 134 extend inwardly so as to guide the tube 130 therebetween. The frame portion 136 is secured to a flat surface 138 at the bottom of the latch mechanism 68. A screw, bolt or other fastener 140 serves to affix the frame portion 136 onto the flat surface 138 of latching mechanism 68. Arm 74 extends resiliently upwardly from the flat surface 138 so as to support hook member 72 at an end opposite the flat surface 138. The button 70 extends outwardly from a surface of the arm 74 between the hook member 72 and the flat surface 138.

Figure 6:
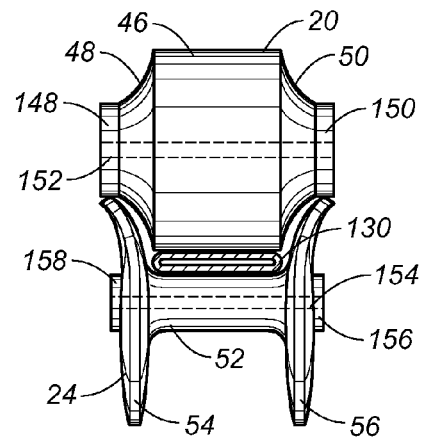
FIG. 6 is an illustration of the meshing of the rollers with each other about a tube therein.

FIG. 6 shows the engagement of wheel 20 with wheel 24. Wheel 20 includes the rubber wheel portion 46 thereon. The beveled surfaces 48 and 50 extends outwardly therefrom so as to taper to a hub portion 148 and 150, respectively. An axle hole 152 extends centrally through wheel 20 so as to rollably support the wheel 20 on the U-shaped brackets of the leaf spring 42. The wheel 24 also includes a central wheel portion 52 that is formed between flanges 54 and 56. The rubber wheel portion 52 is of a relative narrow diameter. Axle hole 154 extends centrally through the rubber wheel portion 52. Hubs 156 and 158 are formed at opposite ends of the wheel 24 on the outside of the flexible flanges 54 and 46.

FIG. 6 illustrates a tube 130 as being compressed between the rubber wheel portion 46 of wheel 20 and the rubber wheel portion 52 of wheel 24. The flexible flanges 54 and 56 will deform outwardly because of contact with the beveled surfaces 48 and 50 of wheel 20. When the tube 130 is suitably compressed, it will urge fluid outwardly in the direction of movement of the shell 12 relative to the tube 130.

Figure 7:
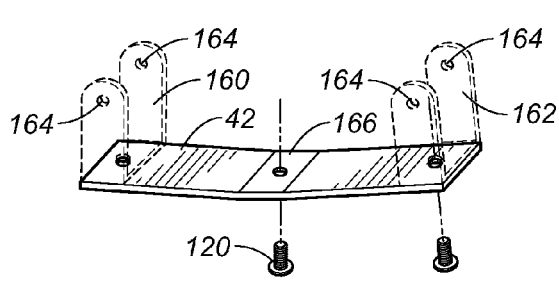
FIG. 7 is perspective view of the leaf spring for securing the wheels within the shell of the present invention.

FIG. 7 shows the leaf spring 42. Leaf spring 42 is secured by the bolt 120 to the upper surface of the first housing 14. U-shaped brackets 160 and 162 are secured at opposite ends of the leaf spring 42. U-shaped brackets 160 and 162 have suitable axle holes 164 respectively formed therethrough so as to receive the axle that supports the respective wheels therein. U-shaped bracket 160 will receive wheel 22 therein. U-shaped bracket 162 will receive wheel 20 therein. As can be seen, the leaf spring 42 is slightly bent at a center 166 thereof so as to achieve the resilient mounting force within the shell 12. As such, any forces imparted upon the U-shaped bracket 162 will be deflected into the U-shaped bracket 160.

Figure 8:
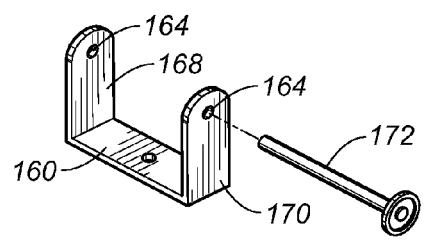
FIG. 8 is an exploded view showing the U-shaped bracket for securing the rollers on the leaf spring.

FIG. 8 shows U-shaped bracket 160. U-shaped bracket 160 is an identical configuration to that U-shaped bracket 162. Axle holes 164 are provided in arms 168 and 170 thereof so as to receive axle 172 therein. The wheel 22 is suitably rotatably supported on axle 172.

Figure 9:
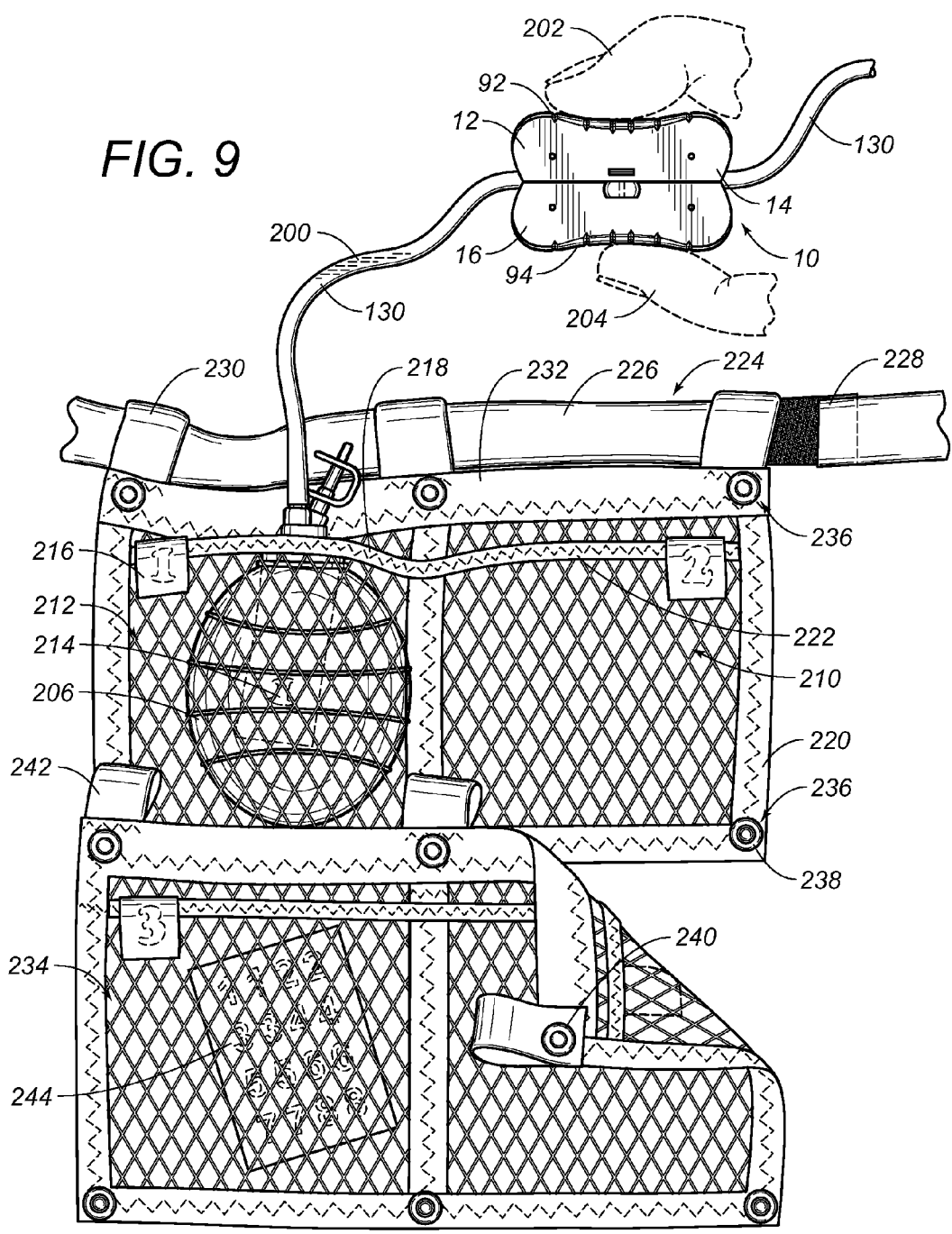
FIG. 9 is an illustration of the bulb-receiving pouch as used in the present invention.

FIG. 9 shows the operation of the apparatus 10 of the present invention as applied to the tubing 130. As such, can be seen, the shell 12 is in its closed position over the tubing 130. Tubing 130 is illustrated as having fluid 200 therein. The top surface 92 receives human thumb 202 thereon. Index finger 204 is applied to the bottom surface 94 of shell 12. The shell 12 is illustrated in its closed position in which the hook member 72 engages slot 76 so as to lock the housing 14 in position over the housing 16. The user will push the apparatus 10 with fingers 202 and 204 toward a fluid-receiving bulb 206 at one end of tube 130. This movement will force the fluid 200 outwardly toward the bulb 206 so as to effectively evacuate the tube 130. It can be seen that the bulb 206 has fluid 200 partially filling the bulb 206.

Importantly, the apparatus of the present invention includes a pouch apparatus 210 which includes a single pouch 212 that receives the bulb 206 therein. The bulb 206 has an alphanumeric indicia 214 affixed thereto. Similarly, the pouch 212 also has an alphanumeric indicia 216 therein. The alphanumeric indicia 214 should correspond to the alphanumeric indicia 216 so that the proper bulb 206 is received in the proper pouch 212. An opening 218 is formed at the top of the pouch 212 so as to allow the bulb 206 to be received therein. Another pouch 220 is secured in side-by-side relationship to the pouch 212. As can be seen, each of the pouches 212 and 220 is formed of a see-through material, such as transparent plastic or mesh material. Pouch 220 also has an opening 222 at a top thereof. Openings 218 and 222 can be suitably elastic so as to allow for flexible receipt of the respective bulbs 206 therein.

The present invention includes a means 224 for securing the pouches 212 and 220 to a human body. As can be seen in FIG. 9, the means 224 is a belt 226 that is suitably elastic so as to extend around a human body. A VELCRO (™) fastener 228 is provided on a surface thereof so as to adjustably affix the belt 226 around the waist of the human body. Suitable loops 230 extend upwardly from the top 232 of the pouches 212 and 220. As a result, the pouches 212 and 220 can slide along the length of the belt 226 so as to fit the needs and desires of the user. A second plurality of pouches 234 are snap fit at button 236 to the side of the pouches 212 and 200 opposite the belt 226. The button fasteners include a female button 238 that engages with the a male button 240. As can be seen, the pouches 234 have a configuration virtually identical to the pouches 212 and 220. Loops 242 are formed along the top edge of the pouches 234. Alphanumeric indicia 244 include labels that are received within the pouches 234 so that the labels 244 can be adhesively adhered to the respective bulb that is received therein. The pouches 212 and 220 also include snap fasteners 246 thereon. The pouch apparatus of the present invention facilitates the ability to secure the various pouches to the human body and to retain the fluid-receiving bulbs in proximity to the human body. As a result, the pouch of the present invention avoids the complicated arrangement of bulbs extending outwardly in a haphhazzard manner from the human body. The device of the present invention facilitates the ability to carry out normal human activity while having the fluid-draining bulbs secured to the body.

Figure 10:
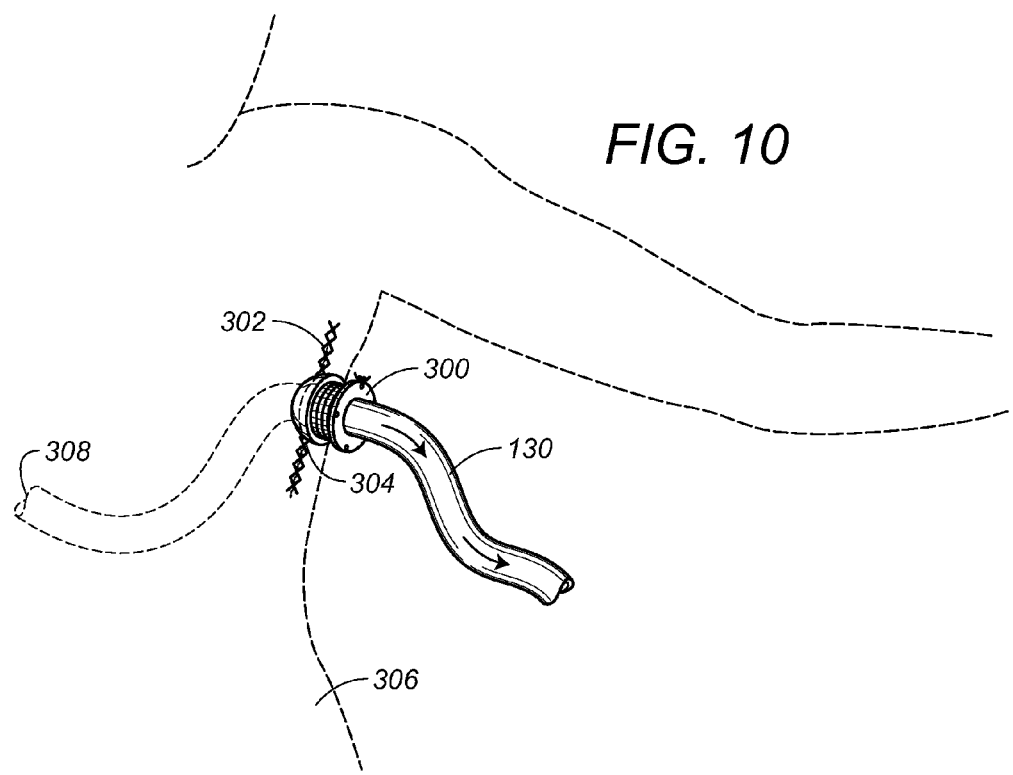
FIG. 10 is a perspective view showing the application of the gasket member of the present invention onto a human body.

FIG. 10 illustrates the opposite end of the tube 130 as having a gasket member 300 that is secured within the stitching 302 associated with an incision 304 on the human body 306. As can be seen, the tube 130 extends through the gasket member 300 so as to have an end 308 terminating in the chest cavity of the human body 306. The stitching 302 is secured to the gasket member 300 so as to firmly affix the gasket member 300 in its proper position against the human body.

Figure 11:
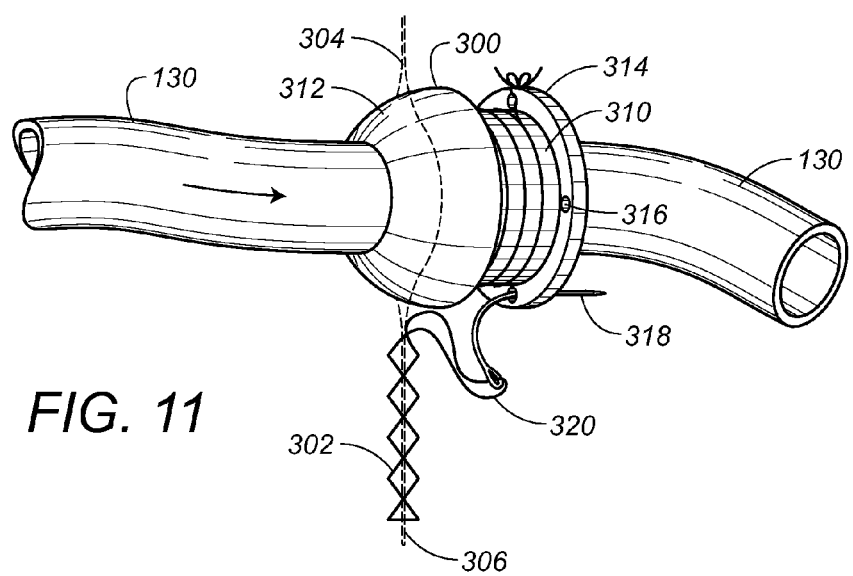
FIG. 11 is a detailed perspective showing the gasket member of the apparatus of the present invention.

FIG. 11 illustrates the manner in which the gasket member 300 is properly secured to the human body 306. As can be seen, the stitching 302 will extend around a notch 310 formed between a concave portion 312 and a peripheral ring 314. The concave portion 312 serves as a sealing contact with the incision 304 on the human body 306. As such, the stitching 302 will effect a proper seal between the concave portion 312 and the human body 306. The peripheral ring 314 includes a plurality of holes 316 formed therearound and therethrough. The holes 316 should having a diameter suitable for allowing a stitching needle 318 to extend therethrough. As can be seen in FIG. 11, the suture 320, which forms the stitching 320, can be introduced through the holes 316 and around the notch 310 so as to effect a positive connection between the gasket member 300 and the human body 306. Since the gasket member 300 is of a more rigid material than is tube 130, the gasket member 300 will not compress when the stitching 302 is tightly wound around the notch 310. As a result, the present invention avoids the difficulties associated with potentially compressing the tube 130 during the stitching of the incision 304. A gasket 300 provides a positive location whereby the stitching can be properly secured in position.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A device for removing fluids from a tube comprising:
   a shell having a first housing and a second housing hingedly connected on a side thereof so as to be movable between an open position and a closed position;
   a first pair of wheels rotatably mounted in said first housing; and
   a second pair of wheels rotatably mounted in said second housing, said first pair of wheels respectively engaging said second pair of wheels when said first and second housings are in said closed position, said shell having an opening at one longitudinal end thereof and an opening at an opposite longitudinal end thereof, each of said first pair of wheels having a generally convex shape, each of said second pair of wheels having a generally concave shape, each of said first pair of wheels having a central rubber wheel portion extending therearound, each of said first pair of wheels having beveled sides extending outwardly on opposite sides of said rubber wheel portion, each of said second pair of wheels having a pair of flexible flanges extending outwardly on opposite sides of a central portion thereof, said beveled sides contacting said pair of flexible flanges when said first and second housings are in said closed position.

2. The device of claim 1, said first pair of wheels being mounted at opposite ends of a leaf spring, said leaf spring secured within said first housing of said shell.

3. The device of claim 2, further comprising:
   a first U-shaped bracket affixed to one end of said leaf spring; and
   a second U-shaped bracket affixed to an opposite end of said leaf spring, one of said first pair of wheels rotatably mounted in said first U-shaped bracket, another of said first pair of wheels rotatably mounted in said second U-shaped bracket, said first pair of wheels being flexibly positioned within said shell.

4. The device of claim 1, each of said openings comprising:
   a first funnel portion formed on one of said first and second housings; and
   a second funnel portion formed on another of said first and second housings, each of said first and second funnel portions forming a funnel having a wide end at the end of said shell extending inwardly and narrowing into an interior of said shell when said first and second housings are in said closed position.

5. The device of claim 1, said shell having a latch means formed thereon, said latch means for releasably retaining said first and second housings in said closed position.

6. The device of claim 5, said latch means comprising:
   a slot formed through a wall of said first housing; and
   an arm with a hook member affixed within said second housing, said arm having a button extending outwardly of said shell, said button movable between a first position allowing said hook member to engage said slot and a second position releasing said hook member from said slot.

7. The device of claim 1, said first housing having a pair of wheel wells formed adjacent opposite ends thereof, said pair of wheel wells corresponding in location to said first pair of wheels in said first housing, said pair of wheel wells accommodating flexible movement of said first pair of wheels in said first housing.

8. The device of claim 7, said shell having a first gripping area defined between said pair of wheel wells on said first housing, said shell having a second gripping area defined on an opposite side of said shell.

9. A device for removing fluids from a tube comprising:
   a shell having a first housing and a second housing hingedly connected on a side thereof so as to be movable between an open position and a closed position;
   a first pair of wheels rotatably mounted in said first housing;
   a second pair of wheels rotatably mounted in said second housing, said first pair of wheels respectively engaging said second pair of wheels when said first and second housings are in said closed position, said shell having an opening at one longitudinal end thereof and an opening at an opposite longitudinal end thereof, and a guide member positioned between one of said first and second pair of wheels in said shell, said guide member having a slot aligned with the pair of wheels, said slot having a width generally matching a diameter of a tube extending between said first and second pairs of wheels.

10. A device for removing fluids from a tube comprising:

a shell having a first housing and a second housing hingedly connected on a side thereof so as to be movable between an open position and a closed position;

a first pair of wheels rotatably mounted in said first housing;

a second pair of wheels rotatably mounted in said second housing, said first pair of wheels respectively engaging said second pair of wheels when said first and second housings are in said closed position, said shell having an opening at one longitudinal end thereof and an opening at an opposite longitudinal end thereof, a tube extending between said first pair wheels and said second pair of wheels when said first and second housings are in said closed position, said tube extending through the openings at said ends of said shell, said first and second pairs of wheels compressing said tube when said first and second housings are in said closed position so as to push fluids outwardly through said tube as said shell moves along a length of said tube;

a fluid-collecting bulb affixed to an end of said tube, said shell movable toward said bulb so as to push the fluids into said bulb;

a bulb-receiving pouch having said bulb removably received therein; and a means for securing said pouch to a human body so as to retain said bulb in proximity to the human body, said pouch comprising:

a first plurality of pouches affixed in side-by-side relation, said means for securing comprising an elastic belt positioned adjacent an upper opening of said first plurality of pouches.

11. The device of claim 10, said bulb comprising a plurality of bulbs, said plurality of bulbs respectively received in said first plurality of pouches, each of said plurality of bulbs having an alphanumeric indicia thereon, each of said first plurality of pouches having an alphanumeric indicia thereon corresponding to said alphanumeric indicia of said plurality of bulbs, said plurality of pouches being formed of a see-through material.

12. The device of claim 10, said pouch further comprising:

a second plurality of pouches removably affixed to an opposite side of said first plurality of pouches from said belt.

13. The device of claim 10, further comprising:

a gasket member affixed adjacent an opposite end of said tube, said gasket member having a concave portion on one side thereof, said gasket member having a notch extending therearound, said gasket member being of a material that has a greater rigidity than a rigidity of said tube.

14. The device of claim 13, said gasket member having a peripheral ring extending outwardly therefrom on a side opposite said concave portion, said peripheral ring having a plurality of holes formed therearound and therethrough, each of said plurality of holes having a diameter suitable for allowing a stitching needle to pass therethrough.

\* \* \* \* \*